United States Patent [19]

Sakai

[11] Patent Number: 4,535,315

[45] Date of Patent: Aug. 13, 1985

[54] ALKANE GAS SENSOR COMPRISING TIN OXIDE SEMICONDUCTOR WITH LARGE SURFACE AREA

[75] Inventor: Sai Sakai, Osaka, Japan

[73] Assignee: New Cosmos Electric Co., Ltd., Japan

[21] Appl. No.: 564,445

[22] Filed: Dec. 22, 1983

[30] Foreign Application Priority Data

Dec. 28, 1982 [JP] Japan ................................ 57-227567

[51] Int. Cl.$^3$ ........................ G01N 27/12; H01L 7/00
[52] U.S. Cl. ........................................... 338/34; 73/23
[58] Field of Search ............. 338/34, 35; 73/23, 27 R; 422/98

[56] References Cited

U.S. PATENT DOCUMENTS

| 4,313,338 | 2/1982 | Abe et al. ............................... 338/34 |
| 4,359,709 | 11/1982 | Nakatani et al. ...................... 338/34 |
| 4,459,577 | 7/1984 | Murakami et al. .................... 338/34 |

FOREIGN PATENT DOCUMENTS

| 53-79600 | 7/1978 | Japan ..................................... 338/34 |
| 55-167174 | 12/1980 | Japan ..................................... 338/34 |
| 55-158547 | 12/1980 | Japan ..................................... 73/23 |
| 56-8538 | 1/1981 | Japan ..................................... 338/34 |

OTHER PUBLICATIONS

Heiland, "Homogeneous Semiconductor Gas Sensors", Sensors & Actuators, vol. 2, No. 4, Sep. 1982, pp. 343-359.

Primary Examiner—Roy N. Envall, Jr.
Assistant Examiner—C. N. Sears
Attorney, Agent, or Firm—Jones, Tullar & Cooper

[57] ABSTRACT

A gas sensor comprising a layer of sintered tin oxide having a large specific surface area and high activity to oxidize and eliminate alcohol, benzene and other miscellaneous gases, whereby the sensor selectively detects alkane gases such as methane gas, propane gas and butane gas. The alkane gas is absorbed thereby decreasing an electrical resistance of the sensor in order to detect the existence of the gas.

3 Claims, 8 Drawing Figures

ALKANE GAS SENSOR COMPRISING TIN OXIDE SEMICONDUCTOR WITH LARGE SURFACE AREA

BACKGROUND OF THE INVENTION

The invention relates to a gas sensor comprising a sintered metal oxide semiconductor and adapted to sense gas leakages of natural gas, liquefied petroleum gas such as methane, butane or propane, namely alkane gases by means of a change in an electric resistance of the semiconductor per se and/or a wire extending therethrough.

Natural gases and liquefied petroleum gases are widely used as fuels for domestic use and industrial uses. There are utilized gas leakage alarming devices made of materials such as sintered metal oxides, for example tin oxide ($SnO_2$) or zinc oxide ($ZnO$) employed to function as sensing elements of the alarming devices.

The known sensing elements comprising the sintered metal oxide semiconductors are however not so selectively sensitive to methane that the alarming devices detect other miscellaneous gases such as hydrogen, carbon monoxide, vapor of alcohol (in particular, ethanol), and cigarette smoke at the same sensitivity as in the case of sensing methane.

Consequently, the known alarming devices are disadvantageous in that they are apt to malfunction due to alcohol vapor liberated from alcoholic liquors used in home cooking or due to sprayed insecticide solution. The other known gas leakage alarming devices equipped in factories or plants are also likely to generate malfunctional alarms caused by exhaust gases emitted from running automobiles or neighboring other factories. It has therefore been tried to solve the above problem, i.e. such a poor selectivity in sensing one of the aforementioned gases which is to be detected to generate an alarming signal. In case of detection of methane gas, it is proposed to coat the sensing element with a layer of one of precious metal catalysts such as platinum and palladium. However, the layers of these precious metals are not only expensive but also considerably deteriorative.

SUMMARY OF THE INVENTION

In view of the drawbacks in the known technology, the invention aims at the provision of a gas sensor which is so selective to a detected gas that any catalyst of precious metal needs not to be coated on a sensing element of said sensor.

The inventor has found a surprising fact that a sintered piece being extraordinarily high in its specific surface area and made of very fine tin oxide powder could be a sufficiently active oxidation catalyst, the activity thereof being enough for catalytic oxidation of some gases such as ethanol vapor. This high catalyzing activity was proved by experiments to have a decisive and favorable influence upon a selectivity of the gas sensor.

The specific surface area of known semiconductors for gas sensors comprising sintered metal oxides such as sintered tin oxide are in general five to twenty (5–20) square meters per gram ($m^2/g$). Such a specific surface area is increased in the invention to a remarkable degree.

Namely, the invention provides a gas sensor comprising a semiconductor composed of a sintered metal oxide selected from a group consisting of sintered tin oxide and sintered zinc oxide, the semiconductor adapted to absorb a gas thereby decreasing an electric resistance of the sensor so as to detect an existence of said gas, characterized in that a specific surface area of the seconductor is thirty square meters per gram or more of said semiconductor, and more particularly fifty to three hundreds (50–300) $m^2/g$. It would be more advantageous in some cases to provide a sintered metal oxide semiconductor with an outer portion having a specific surface area of 50 to 300 $m^2/g$, with an inner portion having a smaller specific surface area.

Thus, an activity of the sintered metal oxide semiconductor is surprisingly improved by decreasing a dimension of fine particles of said metal oxide to a degree such that the specific surface area of the sintered semiconductor becomes greater than 30 $m^2/g$. Owing to the improved activity of said semiconductor, easily combustible or oxidizable gases such as hydrogen and ethanol gas are effectively oxidized within the outer portion of the sintered semiconductor which is not covered with any layer of precious metal catalysts such as platinum or palladium. Consequently, said hydrogen, ethanol and other miscellaneous gases which are not to be detected are prevented from passing through the outer portion into the inner portion of said sintered semiconductor. In other words, concentrations of hydrogen and the other miscellaneous gases are kept at an extremely low level within the inner portion so that these gases cannot be detected by the gas sensor according to the invention.

It will now be clear that the invention provides the gas sensor with a high selective sensitivity for methane, propane, butane and other gases which are relatively difficult to be catalytically oxidized. It is also advantageous that the selective sensitivity of the gas sensor is attained without utilizing any precious metal catalyst such as platinum and palladium.

Other advantages of the invention will become clear in the following description.

BRIEF DESCRIPTION OF THE DRAWINGS

Embodiments are illustrated in the accompanying drawings, in which.

DESCRIPTION OF THE PREFERRED EMBODIMENTS

Figure 1:
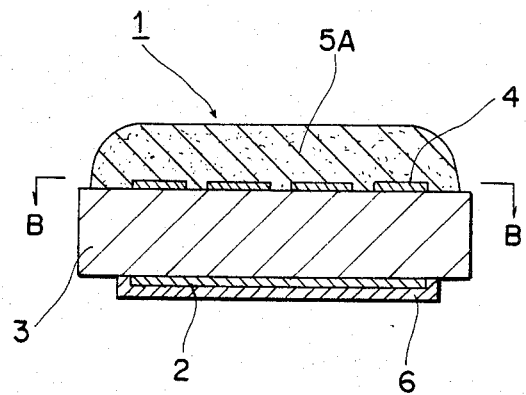
FIG. 1 is a cross section of a gas sensor in an embodiment, the section being taken along line A—A in FIG. 2.
Figure 2:
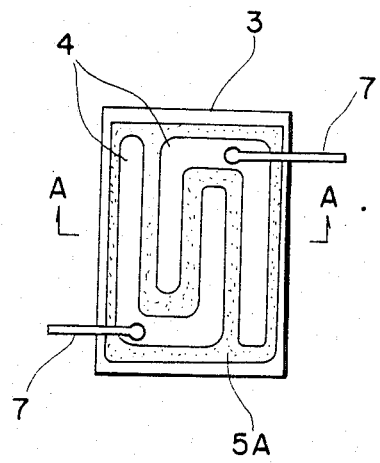
FIG. 2 is a cross section taken along a line B—B in FIG. 1.

Referring now to FIGS. 1 and 2, a gas sensor 1 in an embodiment shown therein comprises a semiconductor piece made of sintered tin oxide. A base plate of alumina 3 of a dimension 1.5×3×0.4 mm carries a thin platinum heater 2 deposited on a lower surface of the base plate. A pair of electrodes 4, 4 are made of thin platinum formed on an upper surface of the base plate 3. A sintered semiconductor 5A covers the electrodes 4 on the base plate. The semiconductor is formed to have a specific surface of 59 m$^2$/g by a process comprising the steps of dispersing an amount of fine tin oxide powder, described hereinafter into ethylene glycol so as to prepare a paste, coating the base plate 3 with the paste to a thickness of about 0.5 mm, drying the coated paste, and sintering at 800° C. for 5 minutes.

The reference numeral 6 indicates an alumina coat embedding the platinum heater 2 whilst the numeral 7 indicates wires each connected to the electrodes 4.

Figure 3:
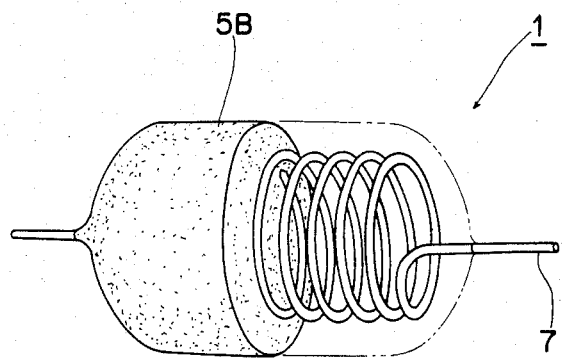
FIG. 3 is a perspective view of a gas sensor in another embodiment with a part cut off.
Figure 4:
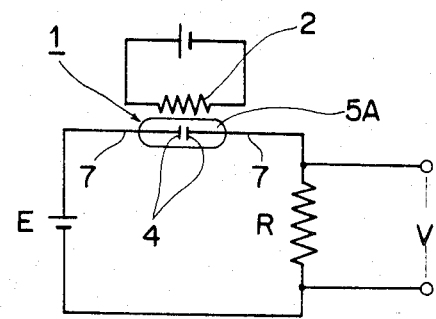
FIG. 4 shows an electric circuit utilized for detection of a gas.

Another gas sensor 1 shown in FIG. 3 comprises a sintered zinc oxide semiconductor 5B which is of a spherical shape and a diameter of about 1 mm. A platinum wire 7 is not connected to any electrode but merely extends through the semiconductor 5B. This sensor does not comprise a base plate. The wire functions also as a heater.

The fine tin oxide powder described above is prepared by a process in which an amount of salt of potassium, calcium, magnesium, silicon or other element is added to a solution of stannic chloride so as to be dissolved thereinto. The said salt functions as an inhibitor controlling the sintering process, described above. An ammonia solution is then dripped into the stannic chloride solution thereby precipitating hydroxide flocks. The flocks are subsequently washed with water, dried and calcinated at 600° C. for 2 hours. Finally, the calcinated flocks are crushed to fine powders which are fine enough to provide the sintered semiconductor with specific surface area of 59 m$^2$/g.

In order to attain such a great specific surface, it is most important to prevent a growth of tin oxide crystallites by means of addition of the inhibitor to an amount of about 0.1% by weight of stannic chloride. The conditions in precipitating and calcinating the hydroxide are also severely controlled.

Figure 5:
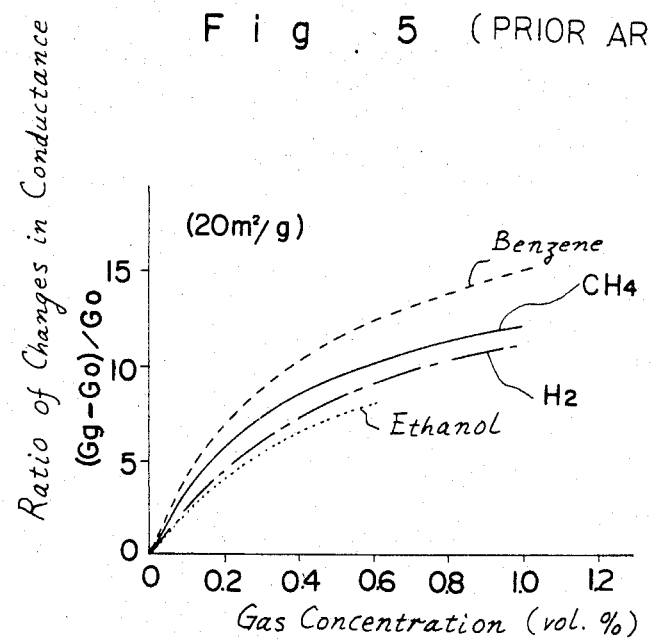
FIGS. 5 and 6 are graphs respectively showing ratios of changes in conductance of a known gas sensor and the invented gas sensor both used for various gases, concentrations thereof being varied within a certain range.
Figure 6:
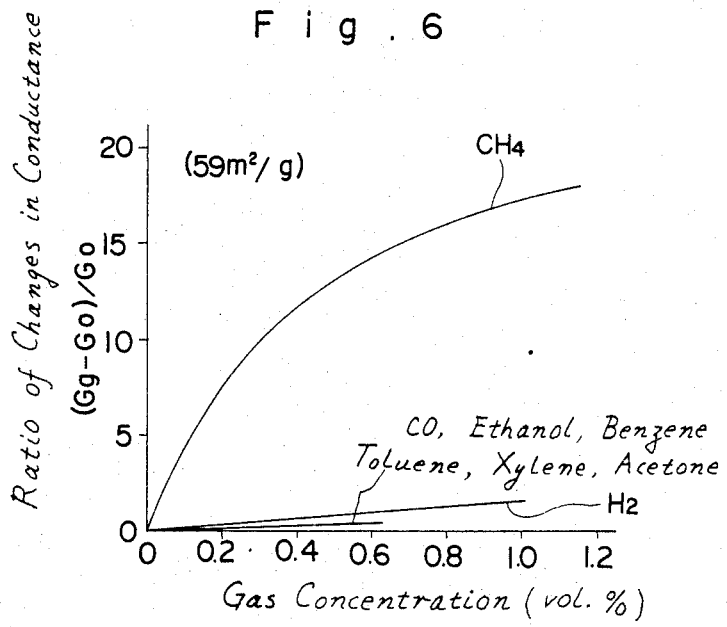

The gas sensor shown in FIGS. 1 and 2 and having a specific surface area of 59 m$^2$/g has different sensitivities for various gases as indicated in FIG. 6. The sensitivities are expressed by means of ratios of changes in conductance of the sensor. On the other hand, a known gas sensor comprising a tin oxide semiconductor of a specific surface area of 20 m$^2$/g has indistinguishable sensitivities for the various gases, as indicated in FIG. 5.

It will be apparent now that the gas sensor according to the invention has a better selectivity for certain gases such as methane because the other gases such as hydrogen, carbon monoxide and alcohol vapor are not detected to give a significant level of output signals.

The ratios of changes in conductance is given by;

$$(Gg - Go)/Go$$

where Go is a conductance before adsorption of gases, and Gg is a conductance after adsorption of gases.

Figure 7:
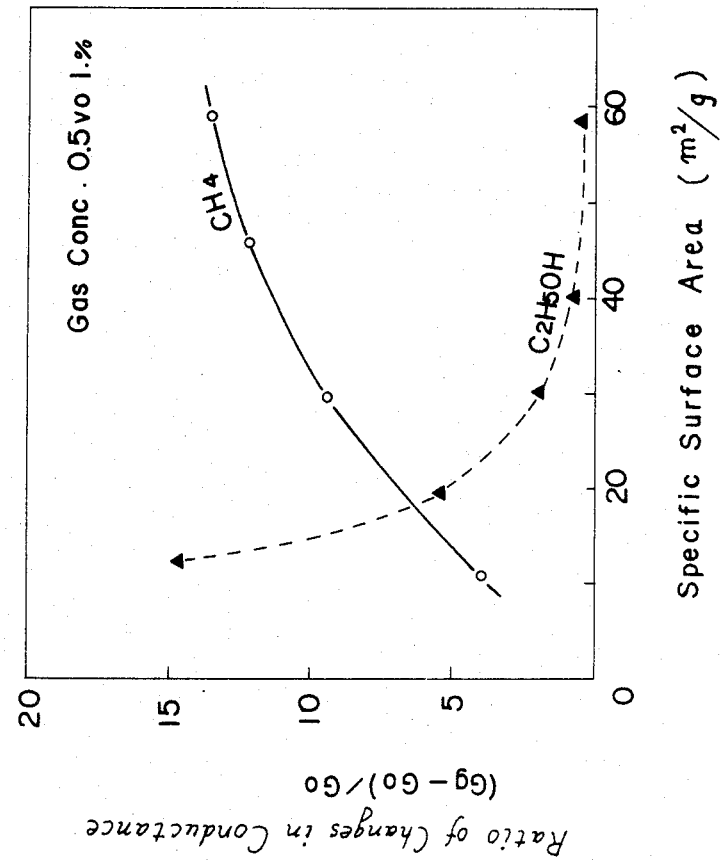
FIG. 7 is a graph showing a relation between selective sensitivity and specific surface area of a sintered tin oxide semiconductor.

The selectivity for the above gases varies with increasing specific surface area as shown in FIG. 7. It will be seen from FIG. 7 that the sintered tin oxide semiconductor is highly selective for methane when the specific surface area is 30 m$^2$/g or more, more desirably within a range between 50 to 300 m$^2$/g. Gas concentrations of methane and ethanol are kept constant during measurement at 0.5% by volume of a tested air sample.

Figure 8:
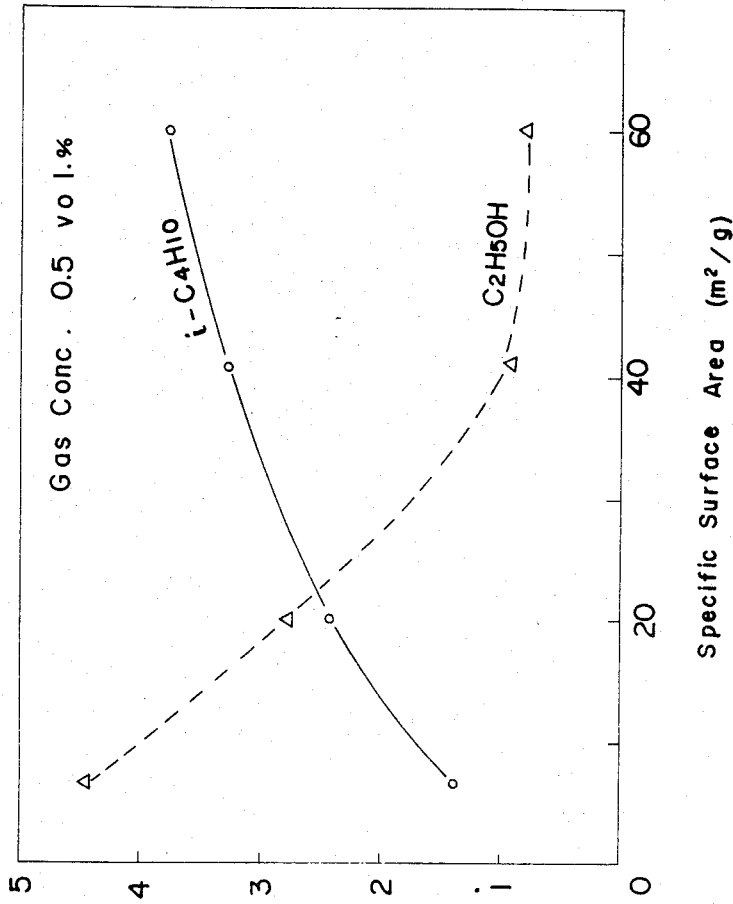
FIG. 8 is a graph showing a relation between selective sensitivity and specific surface area of a sintered zinc oxide semiconductor.

The other gas sensor comprising sintered zinc oxide semiconductor has shown the same characteristic as that of the tin oxide type sensor. Namely, the zinc oxide type sensor also possesses, as shown in FIG. 8, a high selectivity in a specific surface range between 50 and 300 m$^2$/g.

In operation of the gas sensor according to the invention, a voltage of a battery E is charged between the electrodes 4, 4 by interposing a resistor R between one of the electrodes 4 and the battery. If a gas mixture containing methane, hydrogen and ethanol vapor comes in contact with the outer surface of the sintered semiconductor, hydrogen and ethanol are catalytically oxidized by the outer portion of said semiconductor so as not to permeate the inner portion thereof. Thus, only methane which cannot be catalytically oxidized reaches a region of said inner portion located between the two electrodes 4 and 4. An adsorption of methane causes a change in electric resistance of the semiconductor to a degree such that a voltmeter V can detect the adsorption. It will be understood from the above that hydrogen or ethanol does not bring about any hindrance against the detection of methane.

In case of employing the gas sensor shown in FIG. 3, its gas detection mechanism is a little different from that of the previously described gas sensor. When the sintered semiconductor 5B comes in contact with the gas mixture defined above, only methane permeates the semiconductor thereby forming shunts between turns of the coiled wire and increasing heat emission from the semiconductor so as to lower an electric resistance of the wire 7 extending through said semiconductor. This change in resistance, or in conductance defined as a reciprocal thereof, will also be measured by means of the voltmeter V.

The excellent gas selectivity of the sensor will be explained below more in detail.

Hydrogen, carbon monoxide, ethanol, benzene, toluene and similar gases are easily oxidized by a platinum catalyst at a lower temperature, for instance from room temperature to about 130° C. whereas catalytic oxidation of methane is possible at 370° C. That is to say, there is a considerable difference greater than 200° C. in oxidation temperature between the two groups of gases. The sintered metal oxide semiconductor which has a high catalytic activity due to the extraordinarily fine particles thus permits hydrogen, ethanol or other miscellaneous gases to be oxidized effectively but cannot oxidize methane, propane, or other alkane gases. This affords to the gas sensor of the invention such an excellent gas selectivity which the known precious metal catalysts do not possess because of their excessively high catalytic activities.

I claim:

1. An alkane gas sensor comprising a semiconductor composed of sintered tin oxide and adapted to absorb an alkane gas thereby decreasing an electric resistance of the sensor so as to detect existence of said gas, wherein a specific surface area of the semiconductor is at least thirty square meters per gram.

2. A gas sensor as defined in claim 1 wherein the specific surface area of the semiconductor is 50 to 300 square meters per gram.

3. A gas sensor as defined in claim 2 wherein at least an outer portion of the semiconductor has a specific surface area of 50 to 300 square meters per gram.

* * * * *

UNITED STATES PATENT AND TRADEMARK OFFICE
CERTIFICATE OF CORRECTION

PATENT NO. : 4,535,315

DATED : August 13, 1985

INVENTOR(S) : Sai Sakai

It is certified that error appears in the above-identified patent and that said Letters Patent is hereby corrected as shown below:

Column 2, line 2, column 4, line 57, change "absorb" to --adsorb--.

In the abstract, line 6, change "absorbed" to --adsorbed--.

Signed and Sealed this

Twenty-fourth Day of February, 1987

*Attest:*

DONALD J. QUIGG

*Attesting Officer*  *Commissioner of Patents and Trademarks*